United States Patent
Sakurai

(10) Patent No.: US 11,840,166 B2
(45) Date of Patent: Dec. 12, 2023

(54) BOARDING HANDRAIL

(71) Applicant: TOYOTA JIDOSHA KABUSHIKI KAISHA, Aichi-ken (JP)

(72) Inventor: Hideyuki Sakurai, Toyota (JP)

(73) Assignee: TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 414 days.

(21) Appl. No.: 17/363,004

(22) Filed: Jun. 30, 2021

(65) Prior Publication Data
US 2022/0063471 A1    Mar. 3, 2022

(30) Foreign Application Priority Data
Aug. 31, 2020   (JP) .................. 2020-146330

(51) Int. Cl.
*B60N 3/02*  (2006.01)
*A61L 2/10*  (2006.01)

(52) U.S. Cl.
CPC ............. *B60N 3/023* (2013.01); *A61L 2/10* (2013.01); *A61L 2202/16* (2013.01)

(58) Field of Classification Search
USPC ................. 296/1.02; 16/110.1, 412
See application file for complete search history.

(56) References Cited

U.S. PATENT DOCUMENTS

| | | | |
|---|---|---|---|
| 7,175,807 B1 * | 2/2007 | Jones .................... | E05B 1/0069 250/493.1 |
| 9,015,905 B1 * | 4/2015 | Chen .................... | E05B 1/0069 16/904 |
| 11,654,209 B2 * | 5/2023 | Sakurai .................. | A61L 2/10 250/455.11 |
| 11,684,684 B2 * | 6/2023 | De Francesco .......... | A61L 2/22 422/24 |

(Continued)

FOREIGN PATENT DOCUMENTS

| | | | | |
|---|---|---|---|---|
| CN | 104608671 A | * | 5/2015 | |
| CN | 104816663 A | * | 8/2015 | .............. B60N 3/02 |

(Continued)

OTHER PUBLICATIONS

Unpublished U.S. Appl. No. 17/029,044, filed Sep. 23, 2020, 26pp.

*Primary Examiner* — Amy R Weisberg
*Assistant Examiner* — Veronica M Shull
(74) *Attorney, Agent, or Firm* — HAUPTMAN HAM, LLP

(57) ABSTRACT

A boarding handrail includes: an outer pipe which is supported by a support member provided on a periphery of an entrance of a vehicle and of which one segment is removed to form a non-annular shape; an inner pipe that has a substantially C-shaped cross-section as seen from an axial direction, with the outside diameter smaller than the inside diameter of the outer pipe, and is disposed in the one segment by being suspended across one end and the other end of the outer pipe; a sheet member that continuously (Continued)

covers an outer circumferential surface and an inner circumferential surface of the inner pipe and is capable of being moved in a circumferential direction of the inner pipe by a driving device provided inside the inner pipe; and a disinfecting device that is provided inside the inner pipe and disinfects the sheet member by irradiating it with ultraviolet light.

4 Claims, 12 Drawing Sheets

(56) References Cited

U.S. PATENT DOCUMENTS

| | | | | |
|---|---|---|---|---|
| 2014/0137369 A1* | 5/2014 | Street | .................... | E05B 1/0069 16/111.1 |
| 2014/0208541 A1* | 7/2014 | Cowburn | ................ | B25G 1/00 16/110.1 |
| 2014/0322073 A1* | 10/2014 | Link | ........................ | A61L 2/10 250/492.1 |
| 2014/0338153 A1* | 11/2014 | Dopatka | ................... | A61L 2/26 16/110.1 |
| 2017/0333580 A1* | 11/2017 | Cahan | ...................... | A61L 2/26 |
| 2021/0047860 A1* | 2/2021 | Grau | ..................... | E05B 1/0015 |

FOREIGN PATENT DOCUMENTS

| | | | | |
|---|---|---|---|---|
| CN | 110015223 A | * | 7/2019 | ............ B08B 1/006 |
| JP | 2020045027 A | * | 3/2020 | |
| JP | 202063050 A | | 4/2020 | |

* cited by examiner

BOARDING HANDRAIL

CROSS-REFERENCE TO RELATED APPLICATION

This application claims priority to Japanese Patent Application No. 2020-146330 filed on Aug. 31, 2020, incorporated herein by reference in its entirety.

BACKGROUND

1. Technical Field

The present disclosure relates to a boarding handrail.

2. Description of Related Art

There is a hitherto known hanging strap disinfecting device (e.g., see Japanese Patent Application Publication No. 2020-063050). This device includes a light-blocking cover that is provided over an upper part of a handle of a hanging strap, and light emitting elements that are provided inside the cover and capable of emitting ultraviolet light, and disinfects the handle, which is rotatable in a circumferential direction, by irradiating the upper part of the handle covered by the cover with ultraviolet light.

SUMMARY

In the case of a hanging strap, since a passenger grasps the hanging strap by reaching out his or her hand from below, a disinfecting device permanently equipped with a cover as described above also works. In the case of a boarding handrail provided on a periphery of an entrance of a bus etc., however, passengers grasp the boarding handrail from various directions. Thus, a disinfecting device equipped permanently with a cover as described above would make the boarding handrail difficult to grasp and hinder its original function as a boarding handrail.

It is therefore an object of the present disclosure to obtain a boarding handrail that can be disinfected without being hindered from functioning as a boarding handrail.

To achieve this object, a boarding handrail described in claim 1 according to the present disclosure includes: an outer pipe which is supported by a support member provided on a periphery of an entrance of a vehicle and of which one segment is removed to form a non-annular shape; an inner pipe that has a substantially C-shaped cross-section as seen from an axial direction, with the outside diameter smaller than the inside diameter of the outer pipe, and is disposed in the one segment by being suspended across one end and the other end of the outer pipe; a sheet member that continuously covers an outer circumferential surface and an inner circumferential surface of the inner pipe and is capable of being moved in a circumferential direction of the inner pipe by a driving device provided inside the inner pipe; and a disinfecting device that is provided inside the inner pipe and disinfects the sheet member by irradiating the sheet member with ultraviolet light.

According to the embodiment described in claim 1, passengers grasp the sheet member of the boarding handrail when getting on and off the vehicle. Here, the sheet member can be moved in the circumferential direction by the driving device, and also can be disinfected by being irradiated with ultraviolet light by the disinfecting device. Therefore, when passengers are not grasping the sheet member of the boarding handrail, the sheet member can be disinfected while being moved in the circumferential direction. Thus, the boarding handrail can be disinfected without its function being hindered.

A boarding handrail described in claim 2 is the boarding handrail described in claim 1, wherein the driving device is driven to move the sheet member a predetermined amount in the circumferential direction each time the entrance is closed by a door.

According to the embodiment described in claim 2, the sheet member moves a predetermined amount in the circumferential direction each time the entrance is closed by the door. This means that the sheet member is disinfected each time the entrance is closed by the door. Therefore, the sheet member grasped by passengers when they get on and off the vehicle is always disinfected, so that passengers can feel at ease about grasping the sheet member.

A boarding handrail described in claim 3 is the boarding handrail described in claim 1 or 2, wherein the driving device is formed by a pair of rotating members that have sliding resistance on the sheet member, and the rotation speed of one of the rotating members that draws in the sheet member toward the inner circumferential surface of the inner pipe is higher than the rotation speed of the other rotating member that sends out the sheet member toward the outer circumferential surface of the inner pipe.

According to the embodiment described in claim 3, the driving device is formed by the pair of rotating members that have sliding resistance on the sheet member, and the rotation speed of the one rotating member that draws in the sheet member toward the inner circumferential surface of the inner pipe is higher than the rotation speed of the other rotating member that sends out the sheet member toward the outer circumferential surface of the inner pipe. Thus, the sheet member disposed on the outer circumferential surface side of the inner pipe is subjected to tension in the circumferential direction, so that the sheet member is restrained from becoming displaced relatively to the outer circumferential surface of the inner pipe.

A boarding handrail described in claim 4 is the boarding handrail described in any one of claims 1 to 3, wherein the support member supports the outer pipe so as to allow the outer pipe to turn with an axial direction oriented in a vehicle body up-down direction. The outer pipe is configured to protrude toward the outside of the vehicle by turning around a rotating shaft of the support member as a door acts to open the entrance, and to be housed inside the vehicle by turning around the rotating shaft of the support member as the door acts to close the entrance.

According to the embodiment described in claim 4, the outer pipe protrudes toward the outside of the vehicle as the door acts to open the entrance, and is housed inside the vehicle as the door acts to close the entrance. This boarding handrail does not protrude toward the inside of the vehicle (the vehicle cabin side) when assuming a retracted posture. Thus, the boarding space is less restricted by the boarding handrail.

As has been described above, the present disclosure makes it possible to disinfect a boarding handrail without hindering it from functioning as a boarding handrail.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

Figure 1:
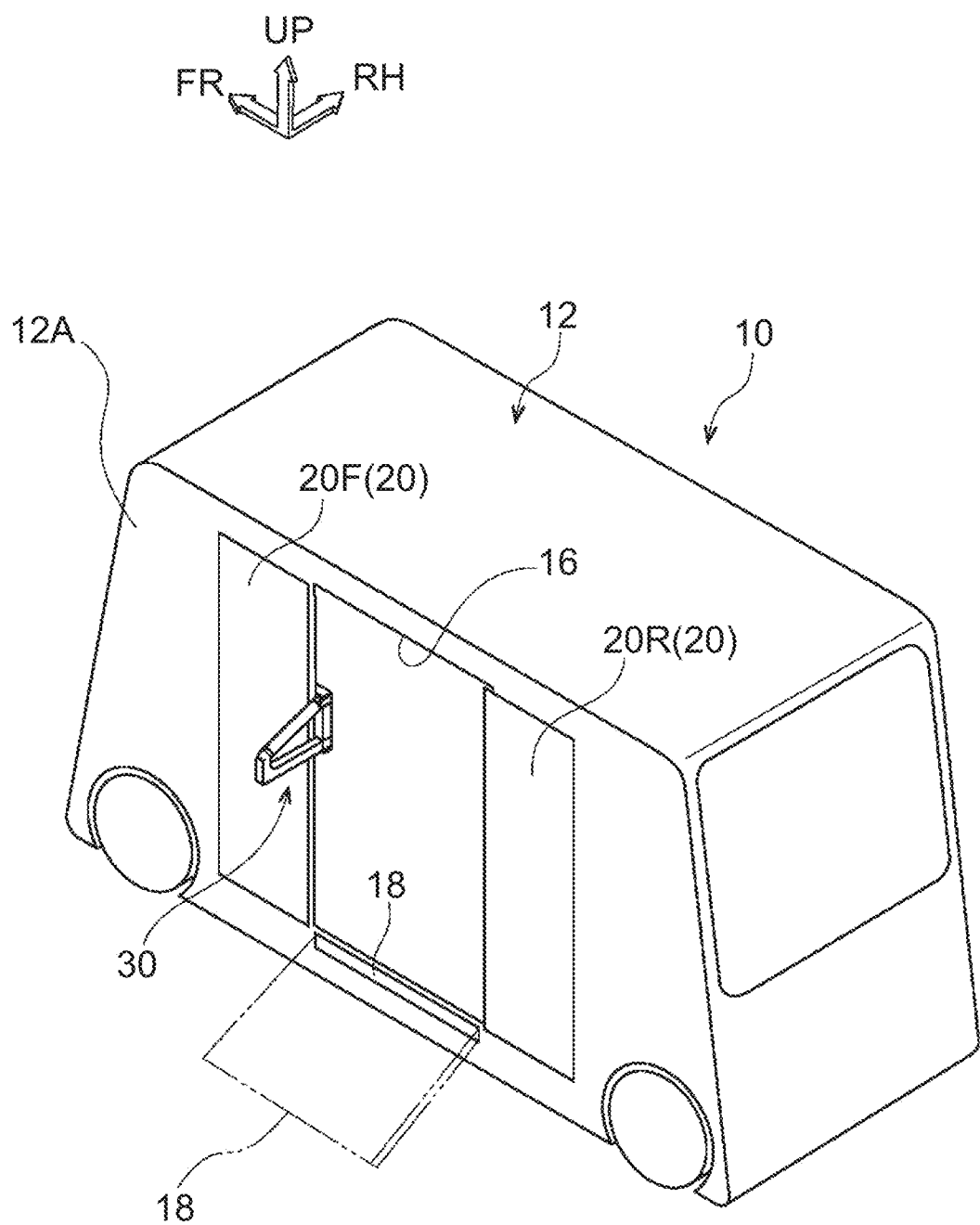
FIG. 1 is a perspective view showing a bus equipped with a boarding handrail according to an embodiment.

Embodiments according to the present disclosure will be described in detail below based on the drawings. A boarding handrail 30 according to the embodiments is suitably provided in a small bus 10 that is one example of passenger-carrying cars as a vehicle (see FIG. 1). (The term "bus" here covers vehicles used for Mobility as a Service (MaaS) represented by a self-driving bus.)

For the convenience of description, arrows UP, FR, LH, and RH shown as necessary in the drawings indicate directions toward a vehicle body upper side, a vehicle body front side, a vehicle body left side, and a vehicle body right side, respectively, of the bus 10. Unless otherwise noted, the directions of up and down, front and rear, and left and right mentioned in the following description mean up and down in a vehicle body up-down direction, front and rear in a vehicle body front-rear direction, and left and right in a vehicle body left-right direction (vehicle width direction).

As shown in FIG. 1, an entrance 16 having a rectangular shape as seen in a side view is formed in a left side wall (one side wall) of a vehicle body 12 of the bus 10, at a substantially central part in the front-rear direction. The bus 10 is provided with a sliding door 20 as a door that opens and closes the entrance 16.

The sliding door 20 is composed of a front-side door half 20F and a rear-side door half 20R each having a rectangular shape of which the length in the up-down direction is longer than the length in the front-rear direction as seen in a side view. The sliding door 20 is configured to be able to open and close the entrance 16 as the front-side door half 20F and the rear-side door half 20R slide (move) synchronously along an outer wall surface 12A of the bus 10 in directions toward and away from each other.

Elastic bodies 22 (see FIG. 10), such as rubber, are attached to end surfaces of the door halves 20F, 20R on inner sides in the front-rear direction (in other words, a rear end surface of the door half 20F and a front end surface of the door half 20R) that come into contact with each other when closing the entrance 16, along the entire end surfaces in the up-down direction. The door halves 20F, 20R close the entrance 16 by bringing their respective elastic bodies 22 into contact with each other so as to elastically deform.

Figure 11:
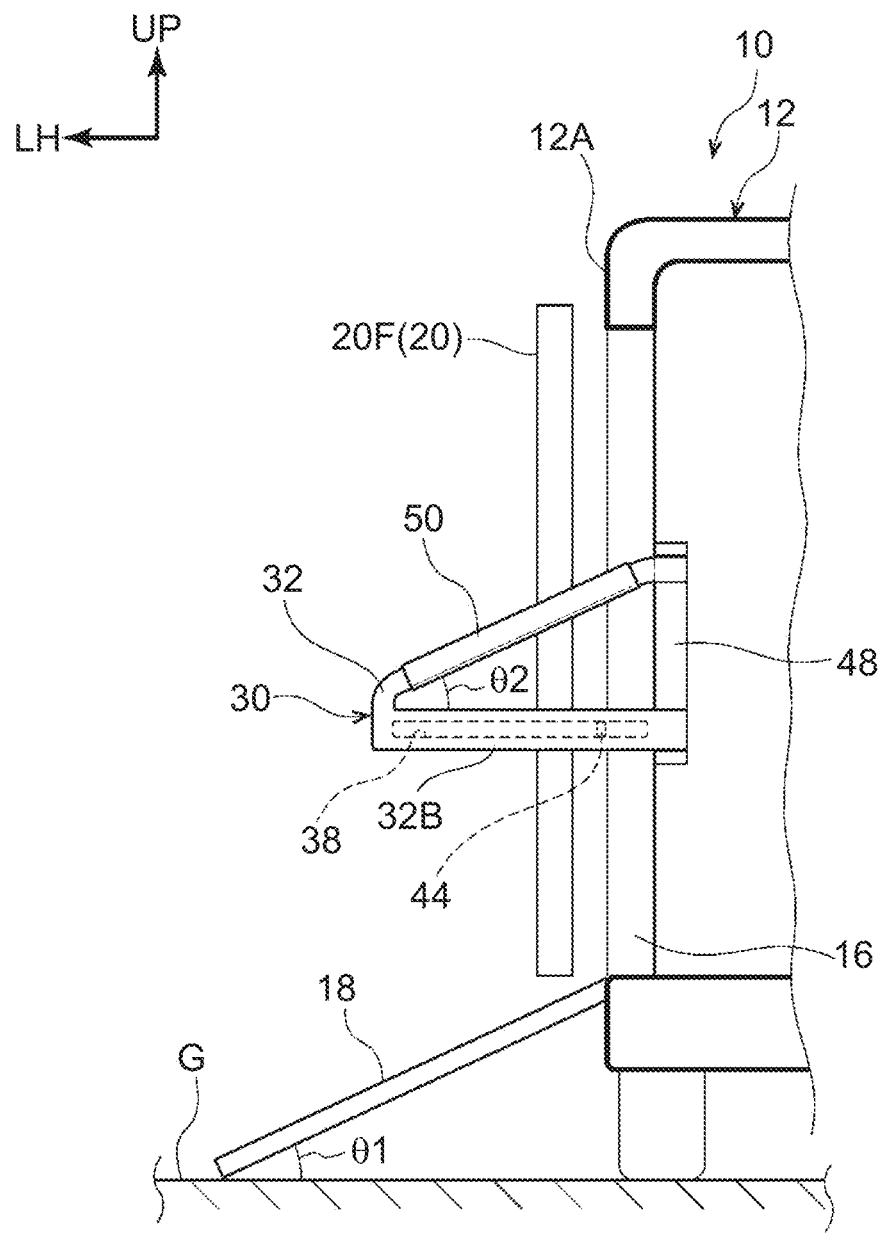
FIG. 11 is a rear view showing a deployed posture of the boarding handrail according to the embodiment.

As shown in FIG. 1, a slope 18 that can be protruded to the outside of the vehicle is housed in the vehicle body 12, under the entrance 16 (e.g., under a floor panel). The slope 18 has a flat plate shape and is configured to be electrically operated to be pulled out and housed. As shown in FIG. 11, when pulled out, the slope 18 is disposed at a predetermined inclination angle θ1 by having a leading end thereof in a pull-out direction supported on a road surface G.

As shown in FIG. 1, when the sliding door 20 (the door half 20F and the door half 20R) slides (moves) and opens the entrance 16, a boarding handrail 30 made of metal (e.g., aluminum) protrudes from a predetermined position in the entrance 16 in the up-down direction (height direction) toward an outer side in the vehicle width direction.

Figure 2:
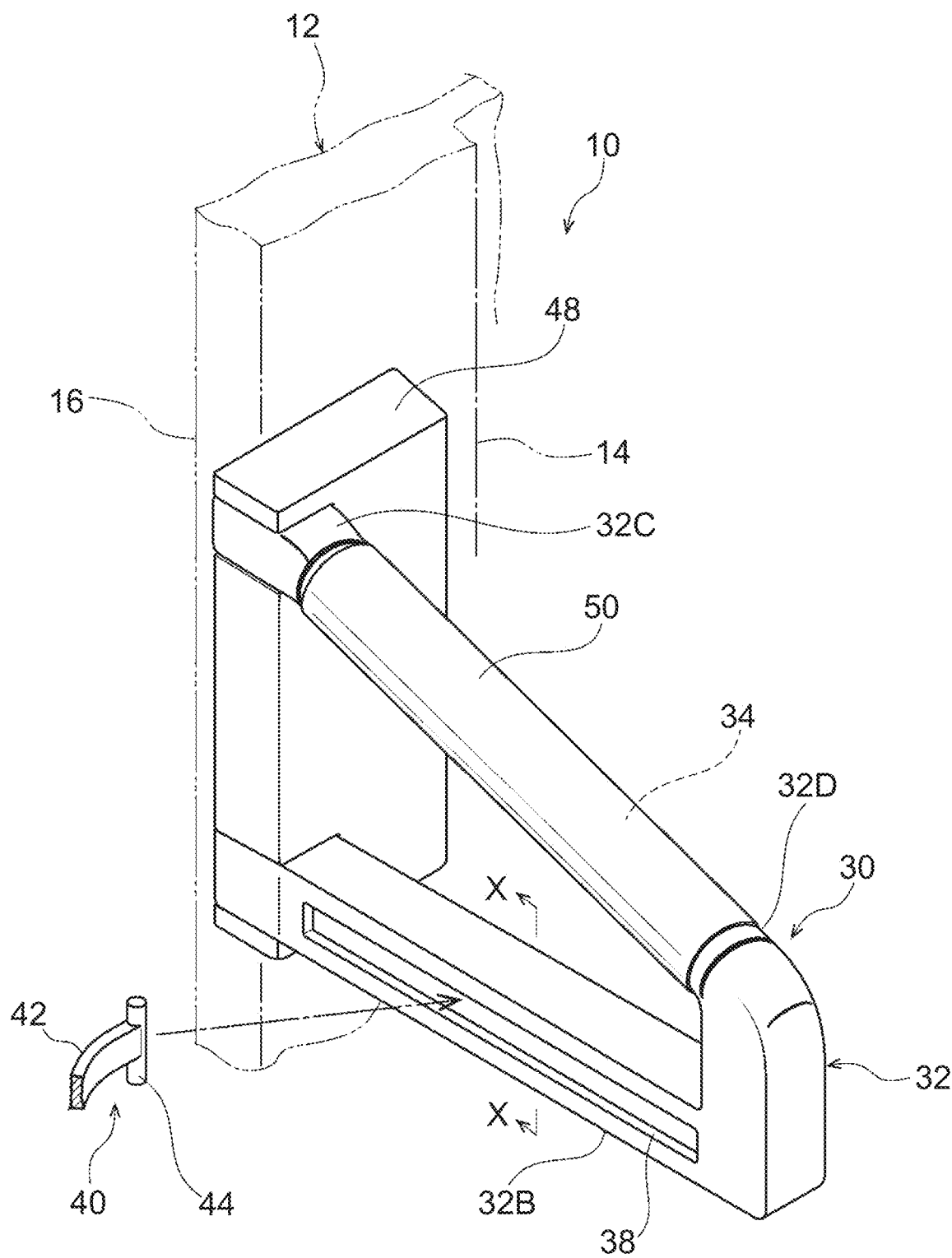
FIG. 2 is a perspective view showing the boarding handrail according to the embodiment.
Figure 6:
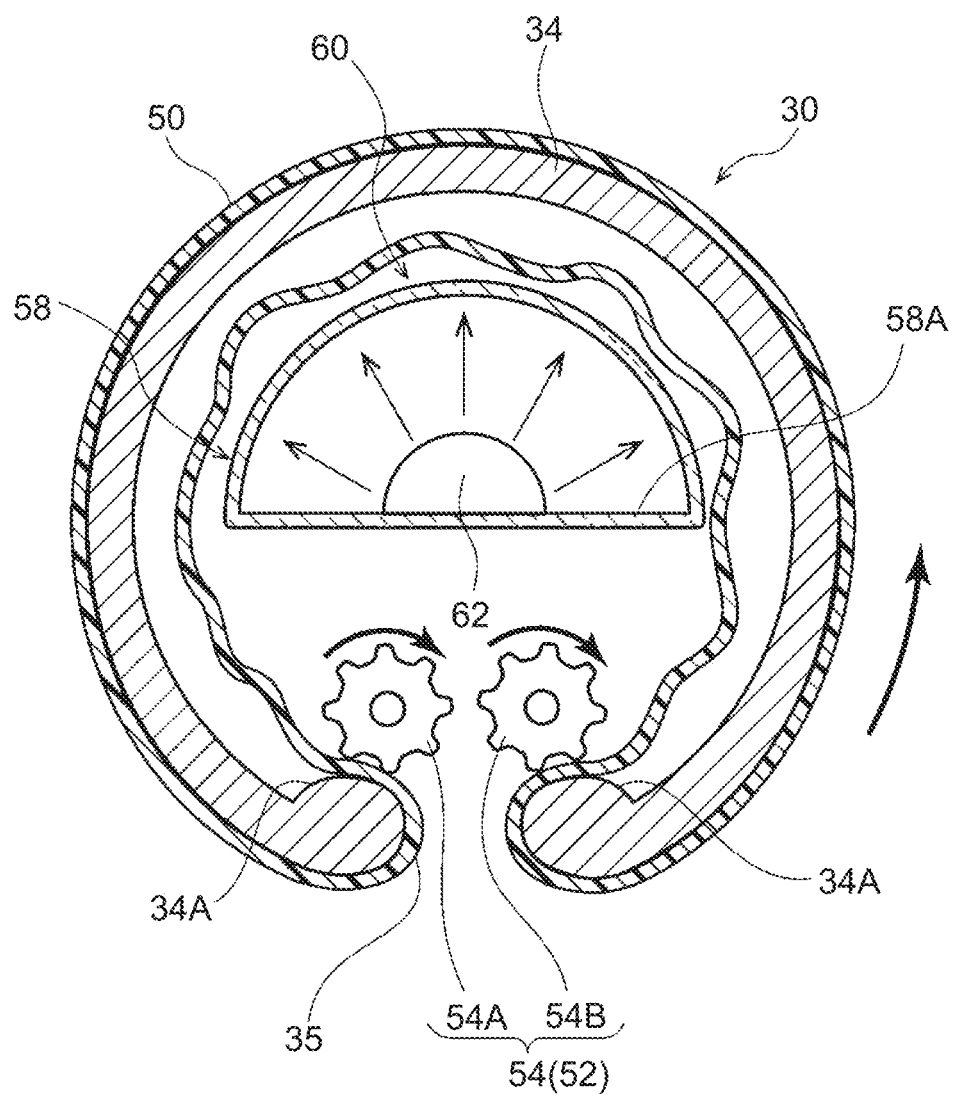
FIG. 6 is a sectional view of an inner pipe of the boarding handrail according to the embodiment as seen from an axial direction.

Specifically, as shown in FIG. 2, the boarding handrail 30 includes a cylindrical outer pipe 32 of which one segment is removed to form a non-annular shape (a substantially C-shape as seen from a direction orthogonal to an axial direction), and an inner pipe 34 that has a substantially C-shaped cross-section as seen from the axial direction as shown in FIG. 6, with the outside diameter smaller than the inside diameter of the outer pipe 32, and is suspended (disposed) in the one segment by having both ends in the axial direction inserted into one open-side end 32C and the other open-side end 32D of the outer pipe 32.

Figure 7:
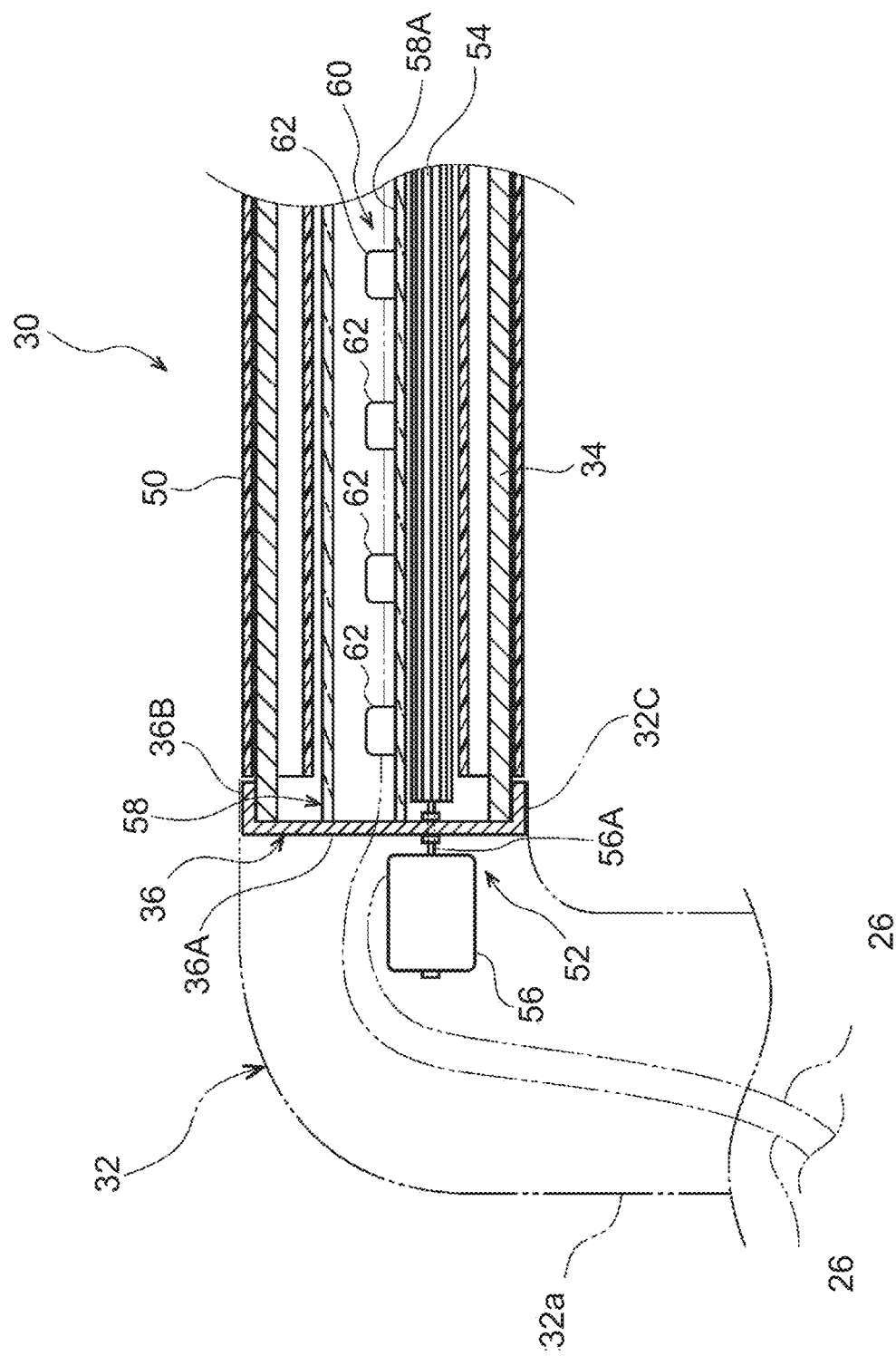
FIG. 7 is a sectional view of the inner pipe of the boarding handrail according to the embodiment as seen from a direction orthogonal to the axial direction.
Figure 8:
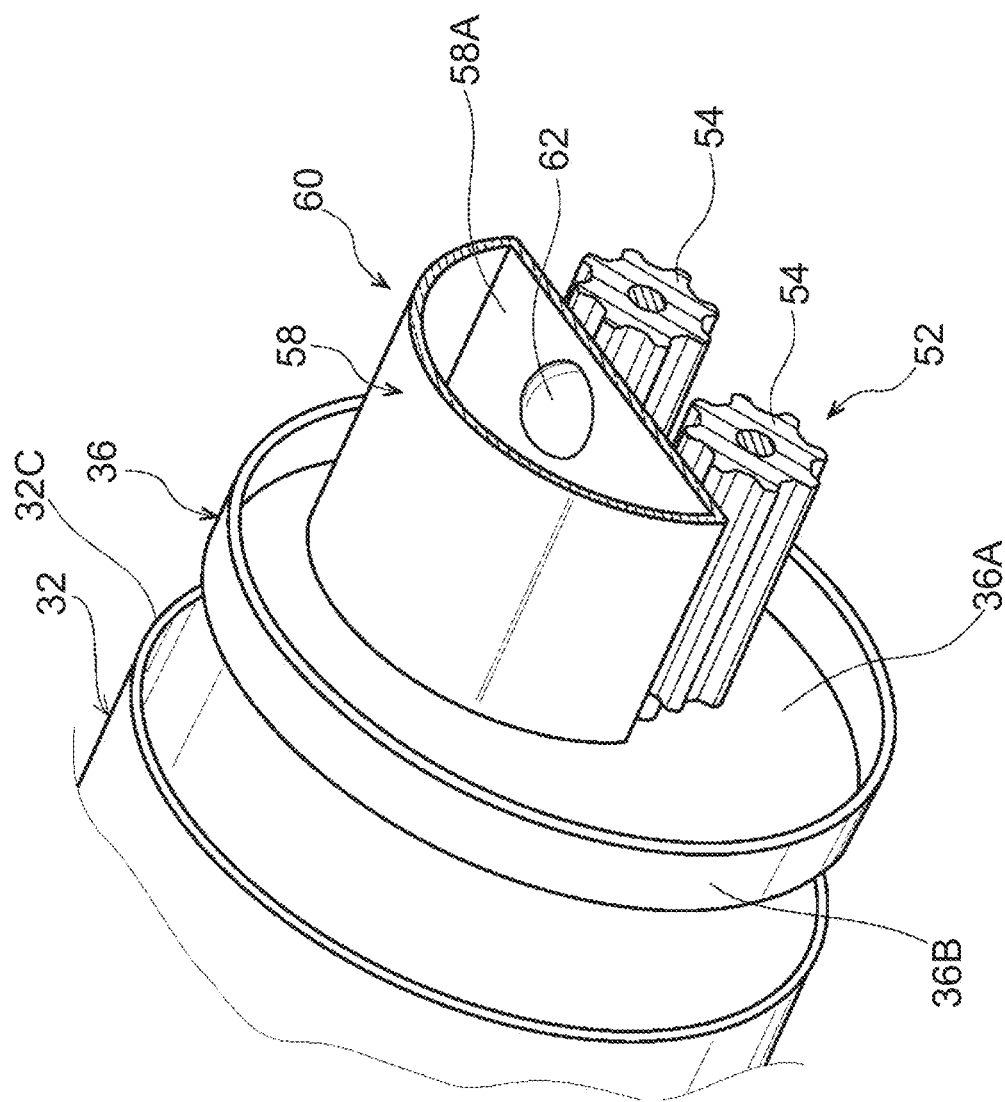
FIG. 8 is an exploded perspective view showing, partially in cross-section, a part where an outer pipe and the inner pipe of the boarding handrail according to the embodiment are fitted together.

As shown in FIG. 7 and FIG. 8, a cap 36 having a shape of a cylinder closed at one end is fitted inside each of the one open-side end 32C and the other open-side end 32D of the outer pipe 32, and both ends of the inner pipe 34 in the axial direction are fitted inside the caps 36. Thus, the inside diameter of the outer pipe 32 is equal to the outside diameter of the cap 36, and the outside diameter of the inner pipe 34 is equal to the inside diameter of the cap 36.

A cylindrical part 36B of the cap 36 that is integrally erected at a circumferential edge of a disc-shaped main body 36A of the cap 36 has a height of about 20 mm. A leading end surface of the cylindrical part 36B and an open end surface of the outer pipe 32 are flush with each other (see FIG. 7). Thus, both ends of the inner pipe 34 in the axial direction are fixed at positions about 20 mm into the one open-side end 32C and the other open-side end 32D of the outer pipe 32. The internal structure of the inner pipe 34 will be described in detail later.

As shown in FIG. 2, the inner pipe 34 extends from an upper part of the outer pipe 32 toward an obliquely lower side. Thus, the inner pipe 34 is disposed so as to be inclined relatively to a horizontal direction, and a right-angled triangle is formed by the inner pipe 34 and the outer pipe 32. As shown in FIG. 11, an inclination angle θ2 of the inner pipe 34 relative to the horizontal direction is set to an inclination angle roughly equal to the inclination angle θ1 of the slope 18.

Figure 5:
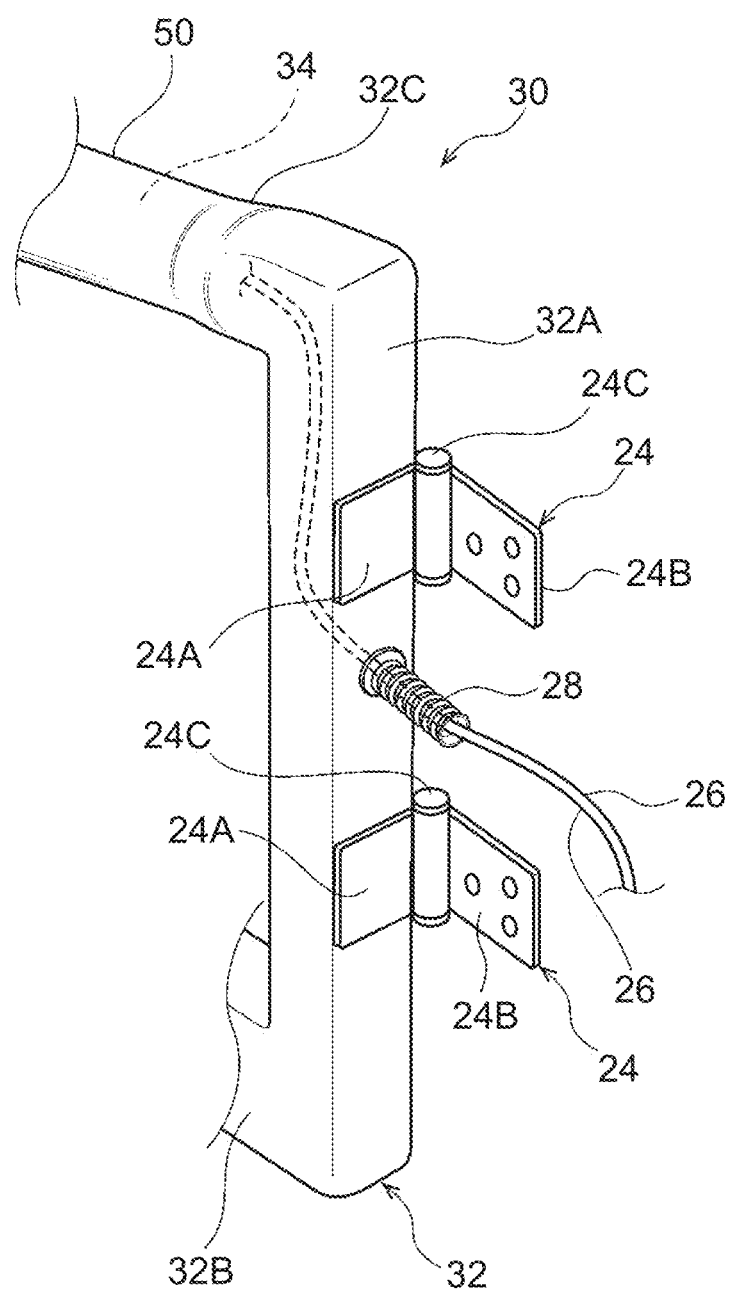
FIG. 5 is a perspective view showing a cable that supplies electricity to light emitting elements and driving motors provided in the boarding handrail according to the embodiment.

As shown in FIG. 5, a base 32A of the outer pipe 32 extending in an up-down direction is supported by a pair of upper and lower metal hinges 24 as support members that are provided on a periphery of the entrance 16 of the bus 10 (e.g., on an inner wall surface of a pillar 14 shown in FIG.

2) such that the base 32A can turn with an axial direction oriented in the up-down direction.

That is, one end part 24A of each hinge 24 is firmly mounted on an outer wall surface of the base 32A by welding or the like, while the other end part 24B of each hinge 24 is firmly mounted on the inner wall surface of the pillar 14 with a plurality of bolts or the like. Thus, the boarding handrail 30 can turn 90 degrees or more around rotating shafts 24C of the hinges 24 as seen in a plan view.

An insertion opening (not shown) for a power supply cable 26 is formed at a central part of the base 32A in the up-down direction (between the upper hinge 24 and the lower hinge 24). The cable 26 is routed from a battery (not shown) installed in the bus 10 so as to pass through the inside of the pillar 14. Then, the cable 26 is inserted into an insertion opening of the base 32A through a supply opening (not shown) formed in the inner wall surface of the pillar 14, and is routed upward through the inside of the outer pipe 32 (base 32A).

The insertion opening of the base 32A is covered with a bellows-shaped rubber boot 28 that is fitted on the cable 26. The hinges 24, a part of the cable 26 exposed between the supply opening and the insertion opening, and the boot 28 are covered with a rectangular box-shaped cover body 48 (see FIG. 2) mounted on the pillar 14.

As shown in FIG. 2, a lower part of the outer pipe 32 is a rail 32B extending in a horizontal direction. The rail 32B slidably holds a sliding member 40 (see FIG. 3) that is mounted at an end of, for example, the door half 20F of the sliding door 20 on the inner side in the front-rear direction.

Figure 4:
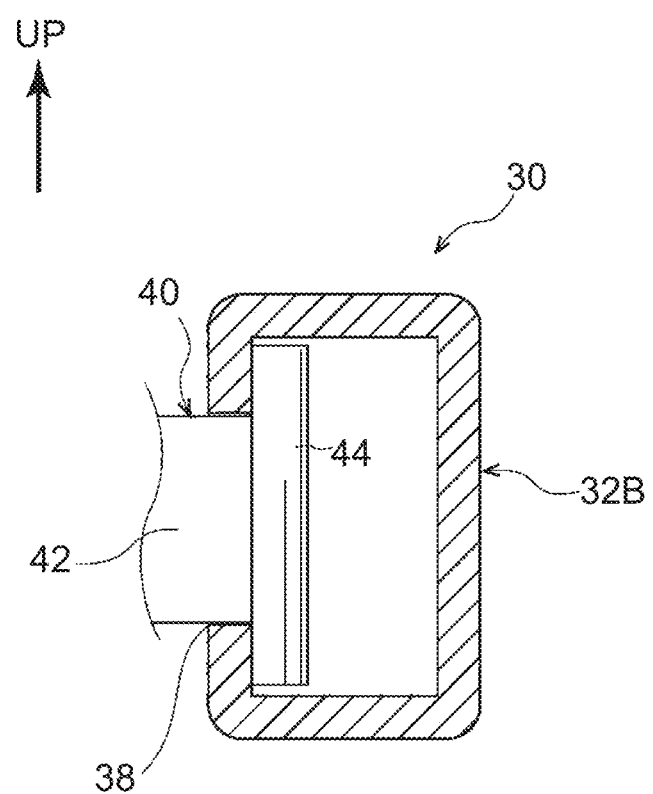
FIG. 4 is a sectional view taken along line X-X of FIG. 2 and seen in the arrow direction, showing a state where the sliding member is held by the rail.

As shown in FIG. 4, the rail 32B has a rectangular tubular shape (a rectangular shape in cross-section) with the long sides oriented in the up-down direction. As shown in FIG. 2, a slit 38 communicating with the inside of the rail 32B and having a predetermined length along an extension direction (longitudinal direction) thereof is formed in one side wall of the rail 32B (the side wall that faces the front side in a deployed posture to be described later and faces the outer side in the vehicle width direction in a retracted posture to be described later), at a substantially central part in the up-down direction.

Figure 3:
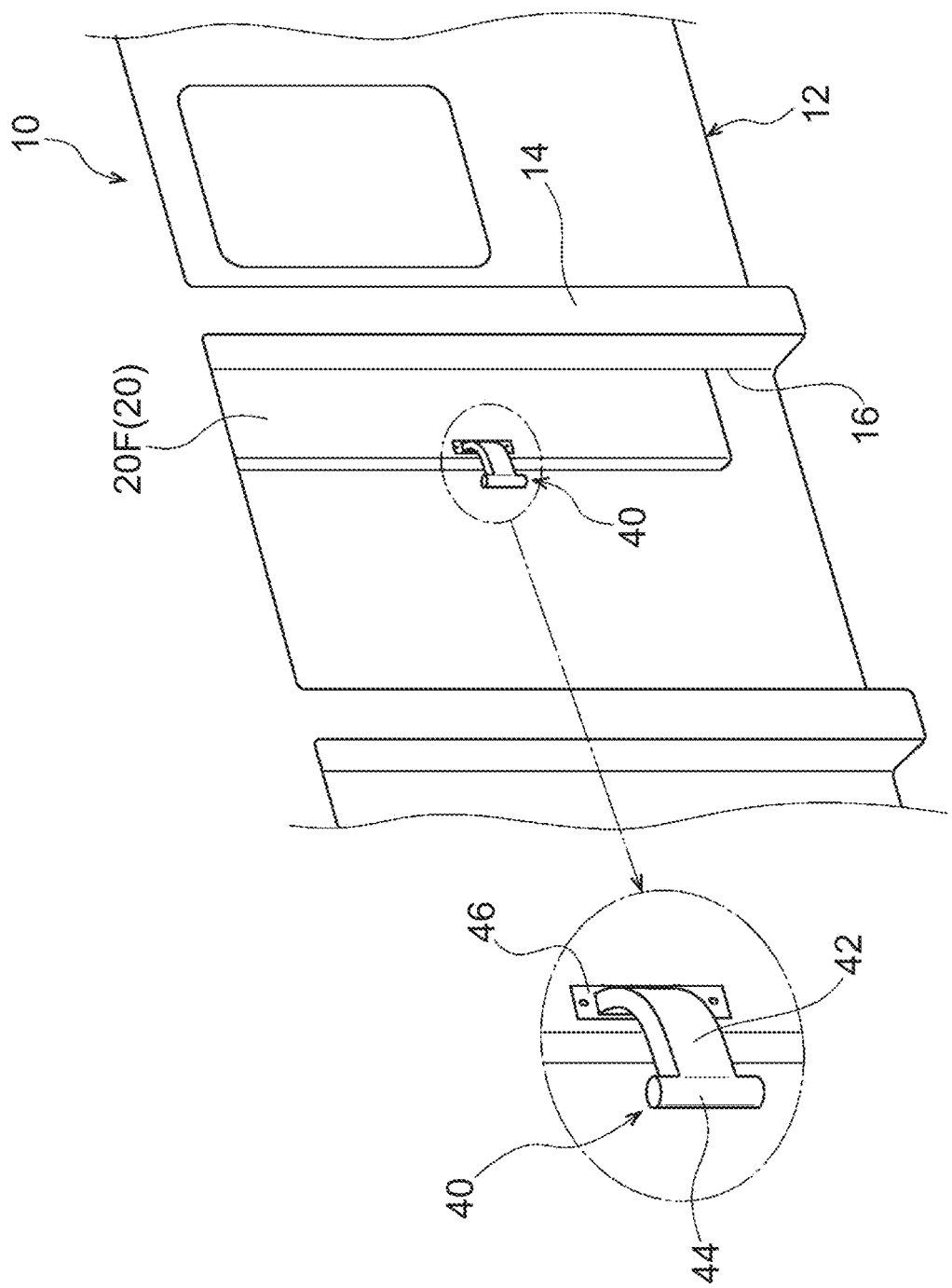
FIG. 3 is a perspective view showing a sliding member that is slidably held by a rail of the boarding handrail according to the embodiment.

As shown in FIG. 3, the sliding member 40 has a substantially T-shape as seen in a side view. That is, the sliding member 40 has a main body 42 that has a curved plate shape as seen in a plan view, a substantially columnar fitting part 44 that protrudes in the up-down direction from a leading end of the main body 42 (has an axial direction oriented in the up-down direction), and a flat plate-shaped fixing part 46 that is formed at a base end of the main body 42 on the opposite side from the fitting part 44.

The sliding member 40 is mounted to the rail 32B before the fixing part 46 is mounted to the door half 20F. Specifically, the fitting part 44 of the sliding member 40 is held laterally (with the axial direction oriented in a horizontal direction) and passed through the slit 38 of the rail 32B and then turned 90 degrees. Thus, as shown in FIG. 4, the fitting part 44 of the sliding member 40 is fitted in the rail 32B so as to be slidable in a longitudinal direction of the rail 32B, without coming off the rail 32B.

Therefore, the width of the slit 38 (the clearance in the up-down direction) is larger than the outside diameter of the fitting part 44 and equal to or slightly larger than the width of the main body 42 of the sliding member 40 (the length of the fitting part 44 along the axial direction as seen in a side view). After the fitting part 44 of the sliding member 40 is fitted in the rail 32B, the fixing part 46 thereof is mounted to the end of the door half 20F on the inner side in the front-rear direction by screw fastening or the like. Thus, the rail 32B is supported also by the sliding member 40.

As shown in FIG. 2 and FIG. 6 to FIG. 8, the inner pipe 34 is provided with a sheet member 50 that covers an outer circumferential surface and an inner circumferential surface of the inner pipe 34 continuously in a circumferential direction. The sheet member 50 is a part that is grasped by passengers and molded from a material having relatively low stretchability, such as a fiber material having water-repellent and antibacterial properties or a rubber material used for medical gloves.

The sheet member 50 is formed to be long enough to cover the entire inner pipe 34 that is exposed from the outer pipe 32, and the thickness of the sheet member 50 is equal to or slightly smaller than the plate thickness of the cylindrical part 36B of the cap 36 (see FIG. 7). The sheet member 50 can be moved in the circumferential direction of the inner pipe 34 by a driving device 52 provided inside the inner pipe 34.

Specifically, bulges 34A that bulge radially inward in a substantially semicircular shape in cross-section are formed at one end and the other end of the inner pipe 34 that define a slit 35 extending in the axial direction (see FIG. 6). The driving device 52 is composed of rotating gears 54 as a pair of rotating members that have sliding resistance (friction) on the sheet member 50 supported on the bulges 34A (that move the sheet member 50 by holding the sheet member 50 between the rotating gears 54 and the bulges 34A), and a pair of driving motors 56 that respectively rotate the pair of rotating gears 54 in one direction.

The rotating gears 54 are respectively rotatably supported on the main bodies 36A of the caps 36 fitted at the one open-side end 32C and the other open-side end 32D of the outer pipe 32, with a rotational axis direction oriented in the axial direction of the inner pipe 34. Thus, the rotating gears 54 extend in the axial direction of the inner pipe 34 and have a length roughly equal to the length of the inner pipe 34.

The driving motors 56 are provided, for example, inside the one open-side end 32C of the outer pipe 32 and supported through a bracket (not shown) on an outer side of the main body 36A of the cap 36 in the axial direction. A rotating shaft 56A of each driving motor 56 is passed through a through-hole (not shown), formed in the main body 36A of the cap 36, and coaxially fixed at a shaft center of the rotating gear 54. Thus, the rotating gears 54 are configured to be rotated in the one direction by a rotation driving force of the driving motors 56.

The rotation speed of one rotating gear 54A that draws in the sheet member 50 toward the inner circumferential surface of the inner pipe 34 is set to be higher than the rotation speed of the other rotating gear 54B that sends out the sheet member 50 toward the outer circumferential surface of the inner pipe 34. Thus, the sheet member 50 disposed on the outer circumferential surface side of the inner pipe 34 is subjected to tension in the circumferential direction, so that the sheet member 50 is less likely to shift relatively to the outer circumferential surface of the inner pipe 34.

Inside the inner pipe 34, a disinfecting device 60 is provided that disinfects the sheet member 50 moving in the circumferential direction by irradiating the outer circumferential surface of the sheet member 50 with ultraviolet light. The disinfecting device 60 is composed of a transparent resin case 58 that has a substantially semicircular cross-section as seen from the axial direction, and a plurality of ultraviolet light emitting elements (hereinafter referred to simply as "light emitting elements") 62 that is provided inside the case 58.

The case 58 extends with a longitudinal direction thereof oriented in the axial direction of the inner pipe 34, and is supported by having both ends in the longitudinal direction joined to an inner side of the main bodies 36A of the caps 36 in the axial direction. The light emitting elements 62 are disposed on a flat part 58A inside the case 58, at predetermined intervals in the axial direction. This configuration allows the outer circumferential surface of the sheet member 50 disposed inside the inner pipe 34 to be irradiated with ultraviolet light evenly in the axial direction and the circumferential direction.

The driving motors 56 and the light emitting elements 62 are supplied with electricity through the cable 26 that is routed through the inside of the outer pipe 32 (see FIG. 7). Therefore, a through-hole (not shown) through which the cable 26 that supplies electricity to the light emitting elements 62 passes (or a wire connected to the light emitting elements 62 is led out) is formed in the main body 36A of the cap 36.

Turning on and turning off the light emitting elements 62 and rotating and stopping the driving motors 56 are controlled by a controller (not shown) that is provided in the bus 10. Specifically, when the controller recognizes that the entrance 16 has been closed by the sliding door 20, the controller issues a signal for supplying electricity to the light emitting elements 62 to turn on the light emitting elements 62, and also issues a signal for supplying electricity to the driving motors 56 to move the sheet member 50 a predetermined amount in the circumferential direction of the inner pipe 34.

The predetermined amount here refers to such an amount that a part of the sheet member 50 having been disposed on the outer circumferential surface of the inner pipe 34 before being moved in the circumferential direction is moved until disposed on the inner circumferential surface of the inner pipe 34. That is, the predetermined amount here refers to such an amount that a front part and a back part of the sheet member 50 replace each other on the inner pipe 34, and this amount is roughly equal to the length in the circumferential direction of a part of the sheet member 50 disposed on the outer circumferential surface of the inner pipe 34 (the length in the circumferential direction of a part of the sheet member 50 disposed on the inner circumferential surface of the inner pipe 34).

The sheet member 50 is moved that predetermined amount (and stopped after the movement) by the controller controlling the number of rotations of each driving motor 56 based on an amount that the sheet member 50 is drawn in by one rotation of the one rotating gear 54A and an amount that the sheet member 50 is sent out by one rotation of the other rotating gear 54B. When the controller recognizes that the entrance 16 is next opened by the sliding door 20, the controller issues a signal for stopping electricity supply to the light emitting elements 62 to turn off the light emitting elements 62.

The boarding handrail 30 is configured such that this process (driving the driving motors 56 to move the sheet member 50 the predetermined amount in the circumferential direction of the inner pipe 34 and turning on the light emitting elements 62) is repeated each time the entrance 16 is closed by the sliding door 20, and that thereby a part of the sheet member 50 that has been grasped by passengers when getting on and off the bus 10 is always sterilized (disinfected) with ultraviolet light. The light emitting elements 62 may be turned off not when the entrance 16 is next opened by the sliding door 20 but when a predetermined time has elapsed with the entrance 16 closed by the sliding door 20.

Next, the workings of the boarding handrail 30 according to the embodiment configured as has been described above will be described.

Figure 9:
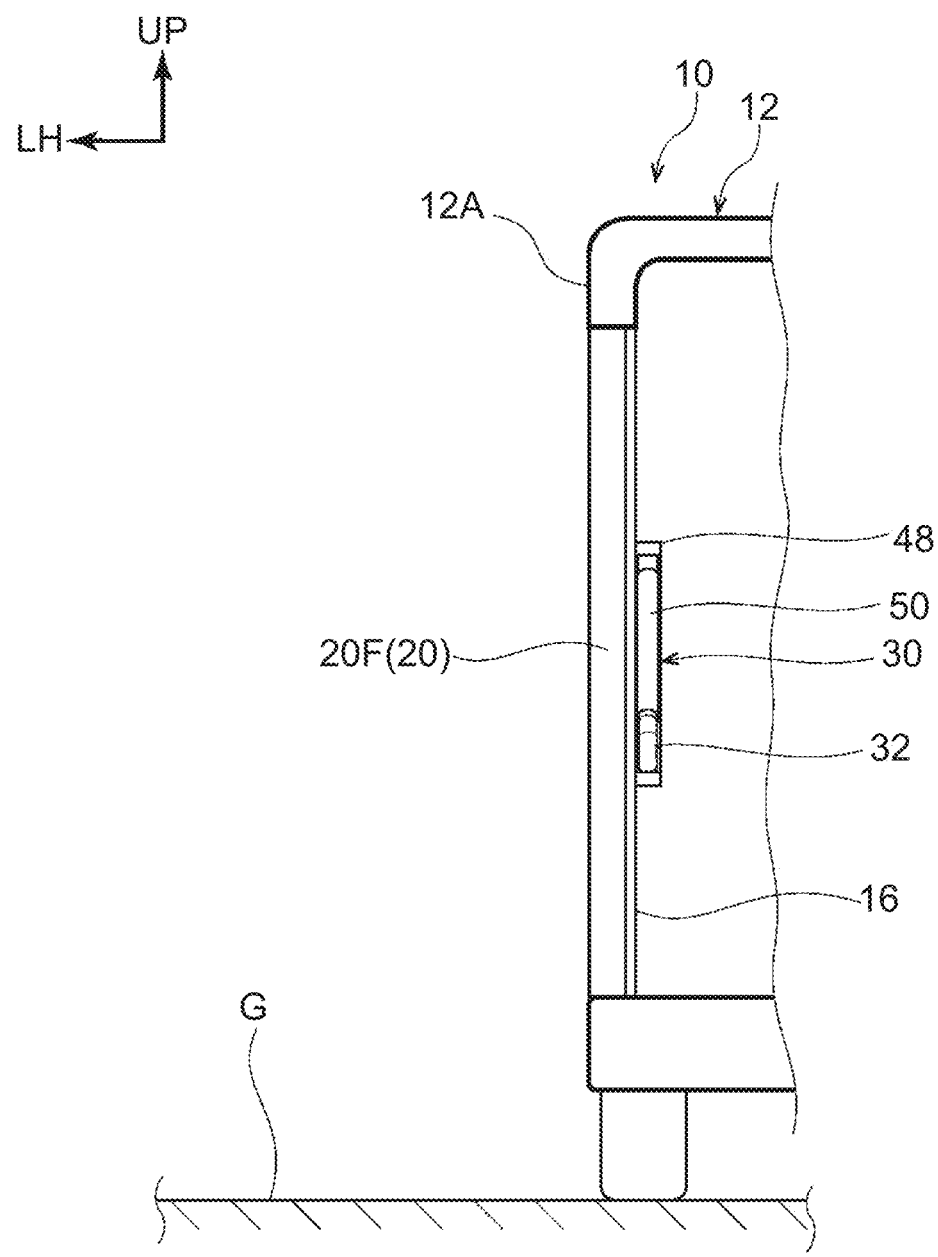
FIG. 9 is a rear view showing a retracted posture of the boarding handrail according to the embodiment.
Figure 10:
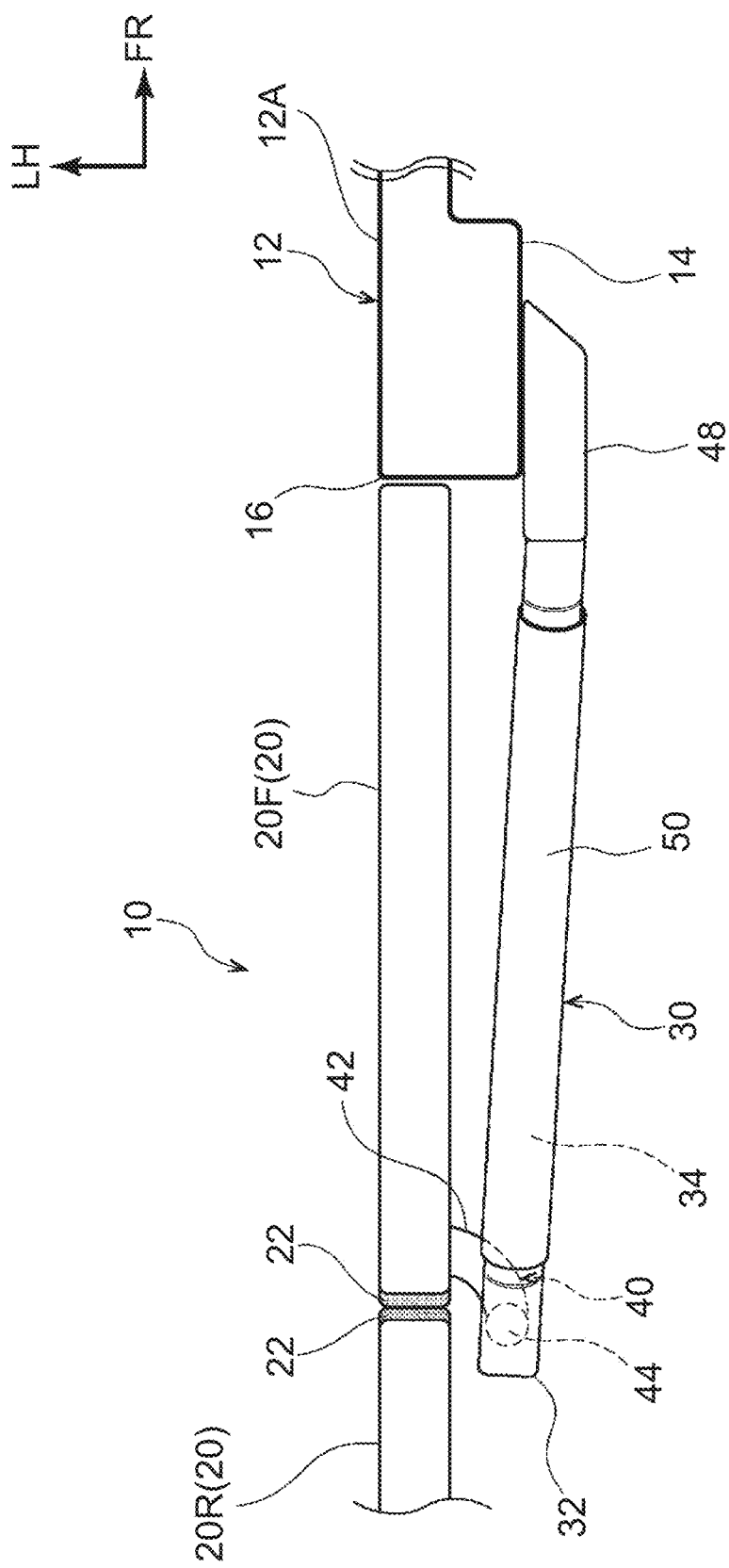
FIG. 10 is a plan view showing the retracted posture of the boarding handrail according to the embodiment.

As shown in FIG. 9 and FIG. 10, when the entrance 16 is closed by the sliding door 20 (door halves 20F, 20R), the boarding handrail 30 is disposed almost along the sliding door 20 (the door half 20F in the case shown) as seen in a plan view. Specifically, when the entrance 16 is closed by the sliding door 20, the boarding handrail 30 assumes a retracted posture in which the sliding member 40 has slid toward the opposite side from the base 32A (toward the other end side) along the rail 32B and the sheet member 50 (inner pipe 34) and the rail 32B are disposed along the sliding door 20.

Thus, when the boarding handrail 30 assumes the retracted posture, the sheet member 50 (inner pipe 34) and the rail 32B do not protrude toward the inside of the vehicle (vehicle cabin side). Therefore, especially in the small bus 10, when the boarding handrail 30 is provided, the boarding space is less restricted (as much boarding space as possible can be secured).

Figure 12:
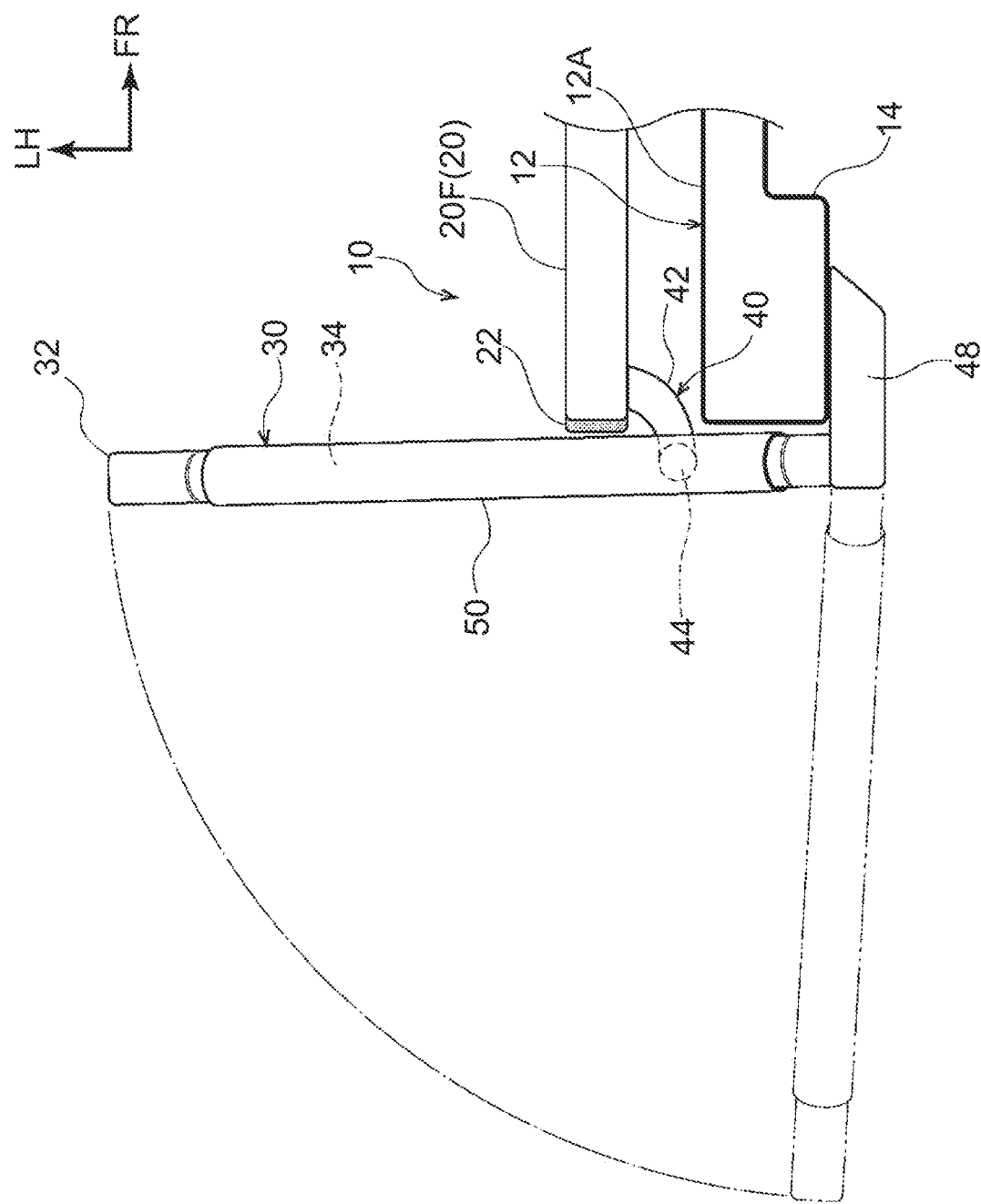
FIG. 12 is a plan view showing the deployed posture of the boarding handrail according to the embodiment.

On the other hand, as shown in FIG. 11 and FIG. 12 when the entrance 16 is opened by the sliding door 20 (door halves 20F, 20R), the boarding handrail 30 protrudes toward the outside of the vehicle as seen in a plan view. Specifically, when the entrance 16 is opened by the sliding door 20, the boarding handrail 30 assumes a deployed posture in which the sliding member 40 has slid toward the base 32A along the rail 32B and the sheet member 50 (inner pipe 34) and the rail 32B protrude toward the outside of the vehicle (the outer side in the vehicle width direction).

Therefore, passengers can grasp the sheet member 50 (inner pipe 34) when getting on and off the bus 10 and thereby easily get on and off the bus 10 (with their posture stabilized). In particular, when getting off the bus 10, passengers momentarily stand on one foot while putting the other foot down. If the sheet member 50 (inner pipe 34) is present on the front side in their advancing direction, it helps passengers stand firmly on one foot and further stabilize their posture.

The sheet member 50 (inner pipe 34) extends from the upper part of the base 32A toward the obliquely lower side. In the case of the bus 10 provided with the slope 18 under the entrance 16, for example, the inclination angle $\theta 1$ of the slope 18 and the inclination angle $\theta 2$ of the sheet member 50 (inner pipe 34) can be set to nearly equal angles (so as to make the slope 18 and the sheet member 50 (inner pipe 34) substantially parallel to each other as seen in a rear view). Thus, when getting on and off the bus 10 using the slope 18, passengers can change the level of their fingers as the level of their body changes, which allows them to easily get on and off the bus 10 while grasping the sheet member 50 (inner pipe 34) (with their posture further stabilized).

When the boarding handrail 30 assumes the deployed posture, a clearance large enough to insert a finger is left between the sheet member 50 (inner pipe 34) and the elastic body 22 attached to the end surface of the door half 20F on the inner side in the front-rear direction. Therefore, even when a passenger inserts a finger between the sheet member 50 (inner pipe 34) and the elastic body 22 (touches the elastic body 22 with a finger) when getting on or off the bus 10 while grasping the sheet member 50 (inner pipe 34), that finger is unlikely to get hurt. Thus, the safety of passengers is secured.

When the controller recognizes that the entrance 16 has been closed by the sliding door 20, the controller performs control to drive the driving motors 56 to rotate, so that the sheet member 50 is moved the predetermined amount in the circumferential direction of the inner pipe 34 and the light emitting elements 62 are turned on. Here, the case 58 is transparent. Therefore, when the light emitting elements 62 are turned on while the sheet member 50 is moved in the circumferential direction, the part of the sheet member 50 that is housed inside the inner pipe 34 is irradiated with ultraviolet light evenly in the axial direction and the circumferential direction.

Thus, the outer circumferential surface of the sheet member 50 having been grasped by passengers before the entrance 16 is closed by the sliding door 20 is sterilized (disinfected) while the sheet member 50 is not grasped by passengers. Moreover, this sterilization of the sheet member 50 is executed each time the entrance 16 is closed by the sliding door 20. Therefore, passengers who get on and off the bus 10 next can grasp the sheet member 50 (inner pipe 34) that is always disinfected and kept clean (with the grasped surface replaced with a clean surface).

In particular, passengers riding the bus 10 can see and learn that the sheet member 50 moves in the circumferential direction, and can thereby recognize that the sheet member 50 is sterilized (disinfected). Therefore, passengers riding the bus 10 can set their mind at ease about grasping the sheet member 50 (inner pipe 34), and can grasp the sheet member 50 (inner pipe 34) without hesitation (at ease). This can further enhance the safety of passengers during getting off the bus 10.

The driving device 52 includes the pair of rotating gears 54 that have sliding resistance (friction) on the sheet member 50 supported on the bulges 34A (that hold the sheet member 50 between the rotating gears 54 and the bulges 34A and send out the sheet member 50). The rotation speed of the one rotating gear 54A that draws in the sheet member 50 toward the inner circumferential surface of the inner pipe 34 is set to be higher than the rotation speed of the other rotating gear 54B that sends out the sheet member 50 toward the outer circumferential surface of the inner pipe 34.

Thus, the sheet member 50 disposed on the outer circumferential surface side of the inner pipe 34 can be subjected to tension in the circumferential direction, so that the sheet member 50 can be restrained from becoming displaced relatively to the outer circumferential surface of the inner pipe 34 when passengers grasp the sheet member 50 (inner pipe 34).

The disinfecting device 60 is provided inside the inner pipe 34. Compared with when a disinfecting device is provided outside the inner pipe 34, the sheet member 50 (the inner pipe 34) can be grasped from various directions. Thus, despite the configuration in which the disinfecting device 60 capable of irradiating the sheet member 50 with ultraviolet light is provided, the boarding handrail 30 is not hindered from functioning as a boarding handrail.

When the controller recognizes that the entrance 16 is next opened by the sliding door 20 after the light emitting elements 62 are turned on, the controller performs control to turn off the light emitting elements 62. This configuration can reduce battery consumption compared with a configuration in which the light emitting elements 62 are kept in a turned-on state also when the entrance 16 is opened by the sliding door 20.

The boarding handrail 30 is not limited to the configuration in which it is provided only on the side of one door half (e.g., the door half 20F) of the sliding door 20. A configuration in which the boarding handrail 30 is provided on both sides of one door half (e.g., the door half 20F) and the other door half (e.g., the door half 20R) of the sliding door 20 may be adopted.

In this case, the boarding handrail 30 provided on the side of the door half 20R is disposed so as to be offset in the up-down direction from the boarding handrail 30 provided on the side of the door half 20F. This is because, due to the structure of the boarding handrail 30, the other end of the rail 32B provided on the side of the door half 20F protrudes toward the door half 20R while the other end of the rail 32B provided on the side of the door half 20R protrudes toward the door half 20F.

That the boarding handrail 30 provided on the side of the door half 20R is thus offset in the up-down direction from the boarding handrail 30 provided on the side of the door half 20F has an advantage in that passengers of various heights can select and grasp the sheet member 50 (inner pipe 34) that suits their own height. Of course, the sliding members 40 respectively mounted on the door halves 20F, 20R are also disposed so as to be offset from each other in the up-down direction according to the positions of the boarding handrails 30.

While the boarding handrail 30 according to the embodiment has been described above based on the drawings, the boarding handrail 30 according to the embodiment is not limited to that shown in the drawings, and design changes can be made thereto as necessary within the scope of the gist of the present disclosure. For example, the support member that turnably supports the boarding handrail 30 is not limited to the configuration using the hinges 24 shown in the drawings, and an arbitrary configuration may be adopted as long as it does not interfere with routing of the cable 26.

The rotating member that moves the sheet member 50 in the circumferential direction of the inner pipe 34 is not limited to the rotating gears 54. The rotating member may be formed by any member that has sliding resistance (friction) on the sheet member 50 supported on the bulges 34A, for example, a rubber roll (not shown) that has no unevenness on the outer circumferential surface. The disinfecting device 60 is not limited to a device composed of the light emitting elements 62, and may be formed by any member that is configured to be capable of emitting ultraviolet light.

Driving of the driving motors 56 and turning on of the light emitting elements 62 are not limited to the configuration in which these are triggered by the controller's recognizing that the sliding door 20 has closed. For example, a configuration in which these are triggered by operation of a switch for closing the sliding door 20 performed by a driver of the bus 10 may be adopted. However, the configuration in which these are triggered by the controller's recognizing that the sliding door 20 has closed can be applied to a self-driving bus on which no driver is present.

What is claimed is:

1. A boarding handrail comprising:
an outer pipe which is supported by a support member provided on a periphery of an entrance of a vehicle and of which one segment is removed to form a non-annular shape;
an inner pipe that has a substantially C-shaped cross-section as seen from an axial direction, with an outside diameter smaller than an inside diameter of the outer pipe, and is disposed in the one segment by being suspended across one end and the other end of the outer pipe;
a sheet member that continuously covers an outer circumferential surface and an inner circumferential surface of the inner pipe and is capable of being moved in a circumferential direction of the inner pipe by a driving device provided inside the inner pipe; and a disinfecting device that is provided inside the inner pipe and disinfects the sheet member by irradiating the sheet member with ultraviolet light.

2. The boarding handrail according to claim 1, wherein the driving device is driven to move the sheet member a predetermined amount in the circumferential direction each time the entrance is closed by a door.

3. The boarding handrail according to claim 1, wherein:
the driving device is formed by a pair of rotating members that have sliding resistance on the sheet member; and
a rotation speed of one of the rotating members that draws in the sheet member toward the inner circumferential surface of the inner pipe is higher than a rotation speed of the other rotating member that sends out the sheet member toward the outer circumferential surface of the inner pipe.

4. The boarding handrail according to claim 1, wherein:
the support member supports the outer pipe so as to allow the outer pipe to turn with an axial direction oriented in a vehicle body up-down direction; and
the outer pipe is configured to protrude toward an outside of the vehicle by turning around a rotating shaft of the support member as a door acts to open the entrance, and to be housed inside the vehicle by turning around the rotating shaft of the support member as the door acts to close the entrance.

* * * * *